United States Patent [19]

Hood, Jr.

[11] Patent Number: 4,848,901
[45] Date of Patent: Jul. 18, 1989

[54] PULSE OXIMETER SENSOR CONTROL SYSTEM

[75] Inventor: Rush W. Hood, Jr., Tampa, Fla.

[73] Assignee: Critikon, Inc., Tampa, Fla.

[21] Appl. No.: 106,747

[22] Filed: Oct. 8, 1987

[51] Int. Cl.[4] .................. G01N 33/49; A61B 5/00
[52] U.S. Cl. ..................................... 356/41; 128/633
[58] Field of Search .............. 356/39, 40, 41, 409; 128/633

[56] References Cited

U.S. PATENT DOCUMENTS

| | | | |
|---|---|---|---|
| 3,638,640 | 2/1972 | Shaw | 356/41 |
| 3,647,299 | 3/1972 | Lavellee | 356/41 |
| 3,847,483 | 11/1974 | Shaw et al. | 356/41 |
| 3,993,047 | 11/1976 | Peek . | |
| 3,994,590 | 11/1976 | DiMartini et al. | 356/409 X |
| 4,001,667 | 1/1977 | Bober | 356/41 X |
| 4,266,554 | 5/1981 | Hamaguri | 356/41 |
| 4,356,448 | 10/1982 | Brogardh et al. | 250/231 R |
| 4,407,290 | 10/1983 | Wilber | 356/41 |
| 4,621,643 | 11/1986 | New, Jr. et al. | 128/633 |
| 4,653,498 | 3/1987 | New, Jr. et al. | 128/633 |

Primary Examiner—Vincent P. McGraw
Attorney, Agent, or Firm—W. Brinton Yorks, Jr.

[57] ABSTRACT

A pulse oximeter is provided including two light emitting diodes. Each LED is energized by a unique modulation signal. Light produced by the LEDs passes through the tissue of a subject and is detected by a photodiode. The photodiode signal is separated by tuned circuits resonant at the two modulation signal frequencies and physiological information signals are recovered from the separated signals by amplitude demodulation. The inventive arrangement provides identification of back-to-back coupled LEDs and narrow band filtering for good noise immunity.

9 Claims, 5 Drawing Sheets

PULSE OXIMETER SENSOR CONTROL SYSTEM

This invention relates to oximeters which measure levels of blood oxygenation and, in particular, to a plethysmograph system for pulse oximetry.

A pulse oximeter measures the oxygen level of blood by transmitting two different wavelengths of light through a portion of a subject's body where arterial blood is flowing. Conveniently this may be a finger or earlobe. The light which has been transmitted through the body is detected by a photodetector, which produces a current that is a function of the pulsatile blood flow. The current produced in response to each wavelength of light is measured, and these measurements may be combined by well-known algorithms such as Bier's Law to produce a quantification of the oxygen content of the blood.

Since the sensor used in the measurement is an electro-optic device, it can respond to interfering signals from the other electrical and optical energy sources. The sensor must respond to changes in light transmissivity through the body. These physiological effects contain frequency components in the DC to 50 Hz band. However, it is desirable that the sensor not respond to ambient light. Accordingly, the plethysmograph system should reject ambient light while detecting physiological signals in the bandwidth of interest.

A second category of sources of interference is other electrical apparatus. Other electrical devices in hospitals, such as electro-surgical instruments, can generate radio frequency signals that a plethysmograph system can pick up. It is desirable then to minimize the sensitivity of the system to interfering signals from sources of this nature.

A known technique for eliminating the interfering signals described above is to drive the light sources by a signal having a frequency which is not present in artificial light or characteristic of other medical instrumentation. Received signals are then passed through a bandpass filter to reject signals outside the band of interest, and the filtered signals are then detected by an envelope detector. While effective for rejecting unwanted signals, the energization of the light sources in alteration by the driving signal mandates that the detector be synchronized with the driving signal for correct demodulation. As the following discusson will show, this arrangement requires undesired widening of the receiver bandwidth, or electrical connections which complicate electrical isolation of the light sources and optical sensor.

In accordance with the principles of the present invention, the response of a plethysmograph system to interfering signals is reduced through modulation of the sensor light sources. The light sources are each modulated with a characteristic that distinguishes received signals from each other and that can be distinguished from ambient light contributions to the detected signal. The deodulation is performed over selective bandwidths which further immunizes the system against radio frequency interference.

In a conventional pulse oximeter sensor a light emitting diode (LED) is used as the light source which transmits light through tissue. Use of an LED is desirable due to its dependability, low voltage requirement, and narrow optical bandwidth of light emission. In accordance with the principles of the present invention, the LED is switched on and off at a frequency which is substantially higher than the frequency range of ambient light (DC) and the physiological signals of interest (DC to 50 Hz). A photodetector receives the transmitted light which further contains a component representative of pulsatile blood flow, the physiological signal, and also receives any ambient light present. The photodetector signal is passed by a bandpass filter which is tuned to a significant component frequency of the switched excitation signal and exhibits a bandwidth similar to that of the physiological signal. The narrow bandwidth enables the system to reject interfering signals at frequencies outside the filter passband, included the substantially constant (DC) component resulting from detection of ambient light. The filter output is a sinusoidal wave, amplitude modulated with the physiological signal. An amplitude demodulator is employed to recover the physiological signal.

The frequency multiplexing technique is a significant improvement over the commonly employed technique of time division multiplexing. In time division multiplexing the LED is similarly switched on and off, and the photodetector signal received when the LED is off, which is caused by ambient light, is subtracted from the signal received when the LED is on. However, due to the need to preserve the phase relationship between the on and off states, the receiver bandwidth must extend from DC to above the excitation signal frequency. Thus, the receiver employing time division multiplexing is responsive to wideband noise over this full bandwidth.

Figure 1:
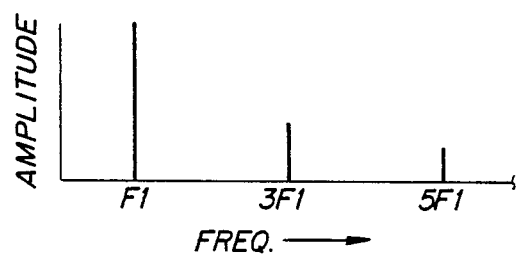
FIGS. 1-3 illustrate spectra resulting from use of the waveform of FIGS. 1a, 1b, 2a, 3a and 6 in frequency multiplexing in accordance with the principles of the present invention.
Figure 1A:
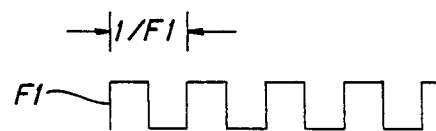
Figure 1B:
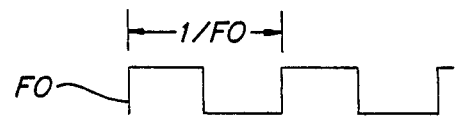

Referring now to FIG. 1, the spectrum of a square wave F1 of FIG. 1a is shown. The spectrum is seen to consist of only odd harmonics of square wave F1, i.e., F1 3F1, 5F1, etc. If the square wave F1 is modulated with a square wave F0, shown in FIG. 1b, the result is the modulated waveform F0×F1 shown in FIG. 2a. This modulated waveform has a spectrum shown in FIG. 2. The spectrum of FIG. 2 consists of the same odd harmonics of the F1 square wave, each with upper and lower sidebands spaced at odd harmonics of F0 from F1, i.e. F1−F0, F1+F0, etc. Neither the harmonics of F1 nor the modulation sidebands occur at frequencies which are even harmonics of F1.

Figure 5:
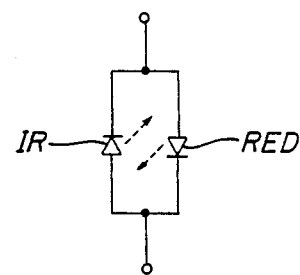
FIG. 5 illustrates a back-to-back configuration of LEDs.

In pulse oximetry it is necessary to use LEDs of two wavelengths in order to gather signal components which can be used to compute blood oxygenation. Conventionally, one LED transmits light at a red wavelength, and the other LED transmits light at an infrared (IR) wavelength. It is convenient to connect the two LEDs in an oximeter sensor in a back-to-back configuration as shown in FIG. 5, allowing either LED to be selectively energized by reversing the applied current and requiring only two connecting conductors. If a differential voltage drive is used, capacitive coupling of the LED drive signals to the detector circuitry, the cable of which is generally in close proximity to the LED conductors, can be minimized. In accordance with the principles of the present invention, one LED will be driven by a signal with the spectrum shown in FIG. 2. The second LED in the sensor is switched by a square wave F2 of a second frequency, which is modulated by the F0 square wave of FIG. 1b. The result of this modulation is the F0×F2 waveform shown in FIG. 3a. This waveform has a spectrum as shown in FIG. 3. The spectrum shows the odd harmonics of F2 and and 3F2, each with upper and lower sidebands spaced at odd harmonics of F0 from F2.

Figure 2:
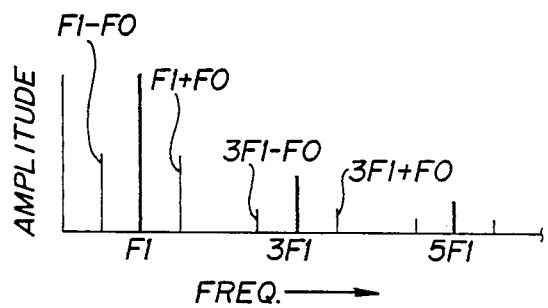
Figure 3:
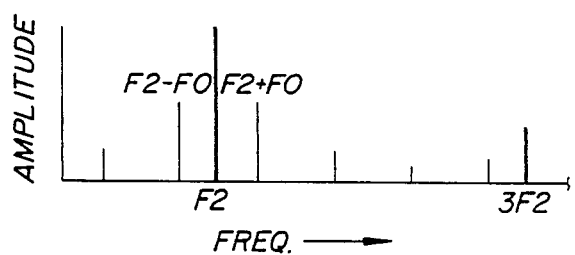
Figure 4:
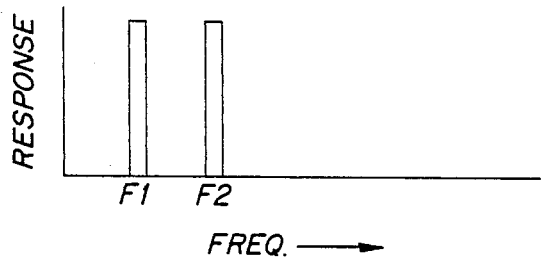
FIG. 4 illustrates a bandpass filter response for the waveforms of FIGS. 2 and 3.
Figure 4A:
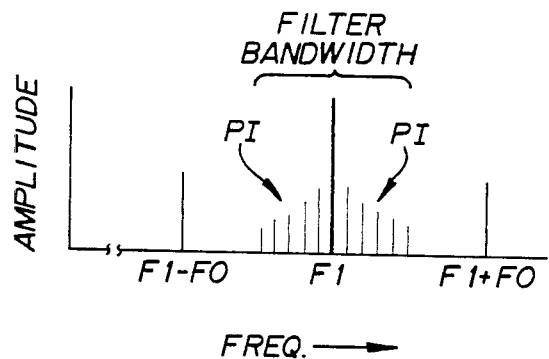

Since the spectrum of FIG. 2 has no components at F2 and the spectrum of FIG. 3 has no components at F1, two bandpass filters can be used to separate the F1 and F2 signal components from the received signal. FIG. 4 shows the responses of two filters that may be used to separate the two desired signals. A bandpass filter centered at F1 will respond to the transmission of light from the LED modulated by the F0×F1 waveform, and a bandpass filter centered at F2 will respond to the transmission of light from the LED modulated by the F0×F2 waveform. Each filter must have a bandwidth of at least twice the bandwidth of the physiological signal, that is, two times 50 Hz=100 Hz, since this information is contained in sidebands of the center frequency. The filter must be narrow enough to exclude the nearest modulation sidebands of the F0 square wave, which are F0 above and below the respective center frequencies of the filters. This is representatively shown in FIG. 4a, which is an expansion of a portion of the spectrum of FIG. 2. This spectrum shows the center frequency F1 of the bandpass filter and the filter bandwidth in the range indicated by the bracket. The F1−F0 and F1+F0 sidebands are outside the filter passband, and the physiological information signals, indicated as PI, are sidebands of the center frequency and contained within the passband.

Figure 2A:
Figure 3A:
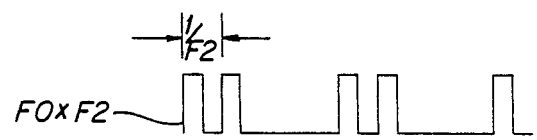
Figure 6:
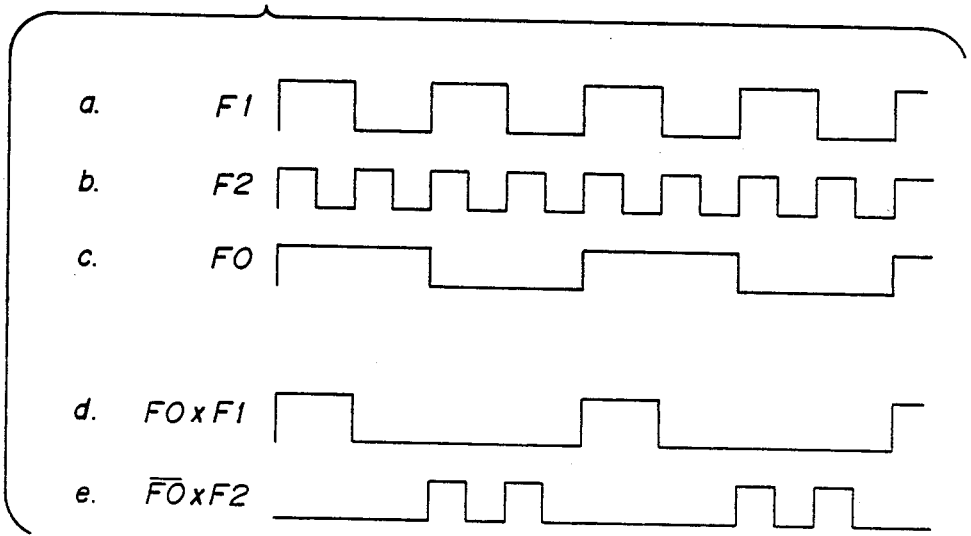

The excitation signal waveforms of FIGS. 2a and 3a are not suitable for use by back-to-back configured LEDs, shown in FIG. 5. This is because the times that the LEDs are on are time coincident, a physical impossibility when the LEDs are so connected. FIG. 6 shows waveforms that exhibit the spectral characteristics of FIGS. 2 and 3 while illuminating only one LED at a time. The square waves F1, F2, and F0 of FIGS. 6a–6c are combined to produce the excitation waveforms of FIGS. 6d and 6e. Specifically, the F0 square wave is used to modulate the F1 square wave such that an excitation pulse is produced each time F0 and F1 are coincidentally high. This produces the excitation waveform F0×F1 shown in FIG. 6d. The inverse of the $\overline{F0}$ square wave, F0, is used to modulate the F2 square wave to produce the excitation waveform $\overline{F0}$×F2 shown in FIG. 6e. Thus, the modulating F0 waveform interleaves the F1 and F2 excitation signals such that there is no time when the two LEDs must be simultaneously turned on.

Figure 7:
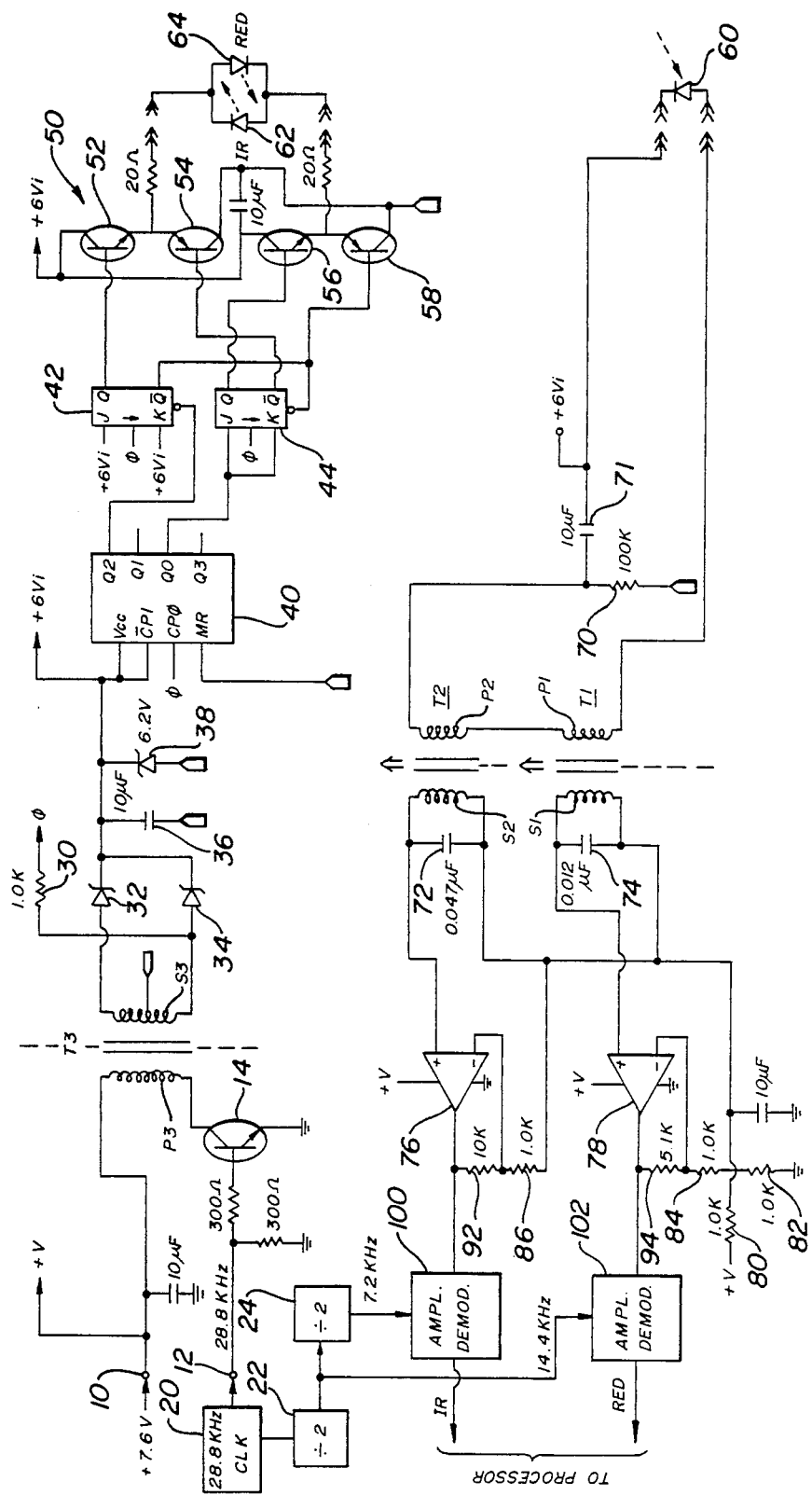
FIG. 7 illustrates a preferred embodiment of the present invention.

Referring to FIG. 7, the modulation and demodulation section and sensor of a pulse oximeter constructed in accordance with the principles of the present invention are shown. In order to minimize electrical hazards to the patient, the sensor electronics are electrically isolated from the electronics of the processor by three transformers T1, T2 and T3. To energize the sensor electronics a 28.8 kHz clock signal is supplied by a source 20 of clock signals to a terminal 12. The 28.8 kHz clock signal switches a transistor 14, which drives the primary winding P3 of transformer T3. A 7.6 volt reference potential is connected to the other end of the primary winding P3 to provide a DC voltage +V for transistor 14 and amplifiers 76, 78, and associated circuits.

The 28.8 kHz signal is transformer coupled to the secondary winding S3 of the transformer T3, which is center-tapped to the isolated ground of the sensor electronics. A resistor 30 is coupled to one end of the secondary winding S3 and provides a 28.8 kHz clock reference signal Φ for the sensor electronics. Rectifying diodes 32 and 34 are coupled to opposite ends of the winding S3 to produce a DC supply voltage +6Vi for the sensor electronics. The rectified supply voltage +6Vi is filtered by a capacitor 36 and stabilized by a Zener diode 38, and is applied at various points to the sensor electronics.

Figure 8:
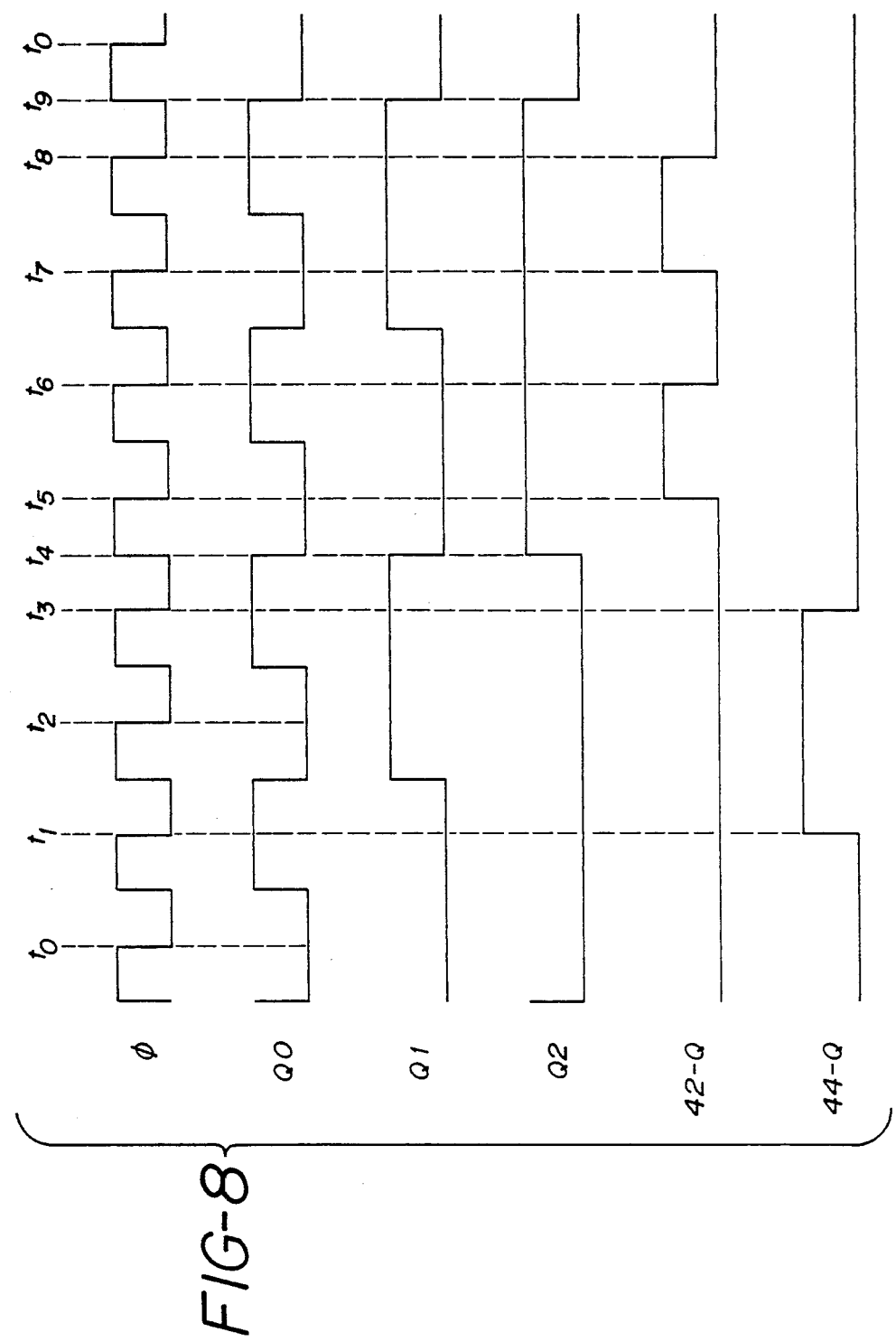
FIG. 8 illustrates waveforms used to explain the arrangement of FIGS. 7a-7b.

The 28.8 kHz reference signal Φ is applied to the input of a three stage binary counter 40 and to the clock inputs of J-K flip-flops 42 and 44. These digital elements cooperate to produce the modulated waveforms which energize LEDs 62 and 64 by way of drive transistors 50 in accordance with the present invention. The counter 40 changes state on the positive-going transitions of the Φ signal and produces square waves at its outputs which are sequentially divided by two. FIG. 8 shows waveforms occurring during one cycle of LED energization. The 28.8 kHz reference signal Φ is shown at the top of the FIGURE. The output signal at the output Q0 of the first counter stage, a 14.4 kHz signal, is shown immediately below in the FIGURE, followed by the 7.2 kHz waveform at the Q1 (second stage) output and the 3.6 kHz waveform at the Q2 (third stage) output. The Q0, Q1, and Q2 output waveforms are all seen to switch on positive-going transitions of the Φ signal.

The Q2 output of the counter 40 is coupled to the reset input of J-K flip-flop 42, and the Q0 output of the counter is coupled to the J and the K inputs of the flip-flop 44. The J and K inputs of flip-flop 42 are coupled to the +6Vi supply voltage, and both flip-flops will accordingly toggle under predetermined conditions. The reset input of flip-flop 44 is coupled to the Q output of flip-flop 42. The J-K flip-flops change state on negative-going clock signal transitions.

Consider first the Q output of flip-flop 44, which is to produce a 7.2 kHz waveform as shown at the bottom of FIG. 8. At the beginning of the LED energization cycle both flip-flops 42 and 44 are reset. The $\overline{Q}$ output of flip-flop 42 is high, and this high signal at the reset input of flip-flop 44 permits the flip-flop 44 to be toggled. The first falling edge of the clock signal Φ at time $t_0$ will not toggle the flip-flop 44 because the Q0 signal at its J and K inputs is low. However, at time $t_1$ the Q0 signal is high, and the negative-going edge of the clock signal Φ will toggle the flip-flop 44 to its set condition. At time $t_2$ the flip-flop will not change state because the Q0 signal is again low. But at time $t_3$ the Q0 signal is again high, and the clock signal Φ toggles the flip-flop 44 to its reset condition. This toggling of flip-flop 44 produces the waveform shown at the bottom of FIG. 8 at the Q output of flip-flop 44, and the inverse at the $\overline{Q}$ output.

During the time that flip-flop 44 is being toggled, flip-flop 42 is inhibited from switching by reason of the low Q2 signal at its reset input. This condition ends at time $t_4$ when the Q2 signal goes high, whereafter the flip-flop 42 may be toggled. Flip-flop 42 is to produce a 14.4 kHz waveform, interleaved in time with the 7.2kHz pulses of flip-flop 44, as shown in the penultimate line of FIG. 8.

At time t5, the clock signal Φ toggles flip-flop 42 to its set condition. The flip-flop 44 will not set at this time because the Q0 signal is low. When flip-flop 42 is set, the low signal at its $\overline{Q}$ output holds flip-flop 44 in its reset condition. At time t6 the clock signal Φ toggles flip-flop 42 to its reset state. Although the Q0 signal is high at this time, the flip-flop 44 cannot be set because the low $\overline{Q}$ signal of flip-flop 42 holds flip-flop 44 in its reset condition during the transition of the clock signal Φ. The simultaneous clocking of the flip-flops by the clock signal Φ sets up a controlled race condition whereby the clock signal Φ cannot toggle flip-flop 44 at the moment of the clock transition by reason of the low signal still at the reset input of flip-flop 44.

At time t7 the flip-flop 42 is toggled again as it was at time t5 and at time t8 the flip-flop 42 is toggled to its reset state as it was at time t6. The flip-flop 44 does not switch at these later times for the same reasons that applied at times t5 and t6. Finally at time t9 the Q2 signal goes low. Flip-flop 42 is once again inhibited and the cycle repeats.

The Q output of flip-flop 42 is coupled to the base of drive transistor 52, and the $\overline{Q}$ output is coupled to the base of drive transistor 58. The Q output of flip-flop 44 is coupled to the base of drive transistor 56 and the $\overline{Q}$ output is coupled to the base of drive transistor 54. The +6Vi supply voltage is applied to the collectors of transistors 52 and 56, which are source transistors for the drive current to LEDs 62 and 64. The collectors of transistors 54 and 58 are coupled to the isolated ground of the sensor electronics so that these transistors may sink LED current. The emitters of transistors 52 and 54 are coupled to each other and to a connector for the LEDs. The emitters of transistors 56 and 58 are coupled to each other and to another LED connector. The back-to-back coupled LEDs 62 and 64 may thus be detachably connected to the respective joined emitters.

In operation, when the Q output signal of flip-flop 42 goes high to drive one of the LEDs with a modulated 14.4 kHz waveform, the Q output signal turns on transistor 52 to provide a current path to the anode of LED 64 and the cathode of LED 62. Transistor 54 is turned off at this time by the high signal from the $\overline{Q}$ output of flip-flop 44, and transistor 56 is turned off by the low Q signal of flip-flop 44. The low Q signal at the $\overline{Q}$ output of flip-flop 42 turns on transistor 58 at this time, and transistor 58 will thus sink the current provided by transistor 52. The flow of current thus is from the +6Vi supply, through transistor 52, the LEDs and transistor 58 to the isolated ground. This direction of current flow will forward bias LED 64, turning it on, and will reverse bias LED 62 and keep it off. LED 64 is accordingly illuminated at the modulated 14.4 kHz rate.

In a similar manner, when the Q output of flip-flop 44 goes high to drive LED 62 with the modulated 7.2 kHz waveform, transistor 56 turns on to source current to the anode of LED 62 and the cathode of LED 64. Transistors 52 and 58 are not conducting at this time by reason of the low and high signals at the Q and $\overline{Q}$ outputs of flip-flop 42. The low signal at the $\overline{Q}$ output of flip-flop 44 turns on transistor 54 to sink current from the LEDs. This path of current will forward bias LED 62 into conduction and reverse bias LED 64, thereby illuminating LED 62 at the 7.2 kHz rate.

The light emitted by the LEDs passes through the tissue of the patient and is received by a photodiode 60.

Photodiode 60 is also detachably connected to the sensor electronics by a connector. The photodiode 60 is energized by application of the +6Vi supply voltage to one side of the connector, with the other side of the connector providing a DC path through the series coupled primary windings P1 and P2 of transformers T1 and T2 and a resistor 70 to the isolation ground. The voltage supply to the photodiode connector is filtered by a capacitor 71.

The photodiode 60 produces an alternating signal in response to the light pulses produced by the LEDs 62 and 64. The alternating signal has two components modulated by physiological information: a 7.2 kHz component developed by the light pulses from LED 62, and a 14.4 kHz component developed by light pulses from LED 64. These two frequency components are separated by transformers T1 and T2. A capacitor 72 is coupled across the secondary winding S2 of transformer T2 to form a tuned circuit resonant at 7.2 kHz. A capacitor 74 is coupled across the secondary winding S1 of transformer T1 to form a tuned circuit resonant at 14.4 kHz. Thus, the composite alternating signal from the photodiode 60 is applied to the primary sides of the two transformers, but their secondary tuned circuits are responsive only to the frequency components corresponding to their respective resonant frequencies. In the preferred embodiment the bandwidth of each tuned circuit is approximately 60 Hz to respond to those signals in the physiological band of interest while providing immunity to out-of-band interference. The transformer coupling provides DC isolation between the sensor electronics and the processor electronics.

The two tuned circuits are coupled to the noninverting inputs of respective amplifiers 76 and 78. The amplifiers have gain determining resistors 84, 86, 92, and 94 coupled to provide negative feedback, and the two amplifiers are DC biased by resistors 80 and 82, coupled between the +V voltage supply and processor ground. The resistor network also provides a DC reference to the side of each tuned circuit opposite the inputs to the amplifiers. The amplifier 76 provides amplified 7.2 kHz signal components and physiological information signals at its output, and the amplifier 78 provides amplified 14.4 kHz signal components and physiological information signals.

The amplified signal components are then demodulated by amplitude demodulators 100 and 102 to recover the physiological information. The 28.8 kHz clock signal is divided by a divider 22 to produce a 14.4 kHz mixing signal for demodulator 102, thereby enabling detection of the amplitude modulated physiological information signals from LED 64. The signal provided by divider 22 is again divided by two by divider 24 to produce a 7.2 kHz reference signal for demodulator 100. This enables demodulation of the amplitude modulated physiological information signals from LED 62. The demodulated information signals, termed RED and IR in the drawing, may then be further filtered to remove the mixing signals and transmitted to the oximeter processor for calculation of the level of blood oxygenation.

It is seen that the arrangement of FIG. 7 provides the modulated LED drive signals on the DC isolated (sensor) side of transformer T3. Separation of the two desired signal components is done through the tuning of transformers T1 and T2, which likewise provide DC isolation for the sensor. It may be appreciated that if the states of the LED drive signals (specifically Q2) were known on the processor side of the transformers, a single demodulator could be used to demodulate the received signals in a time division multiplexing manner. However, coupling this information back to the demodulator would undesirably require a further transformer. The arrangement of FIG. 7 preferably provides all signal requirements and DC isolation with only three transformers. Insofar as the processor side is concerned, transformer T3 provides an energization signal and a free running clock signal to the isolated sensor electronics. The LED drive signals are modulated in asynchronism with respect to the processor side of the system, and LED wavelength discrimination is performed by the resonant secondaries of transformers T1 and T3. No other decoding or discrimination between the isolated sections of the arrangement is required.

What is claimed is:

1. An oximeter system, including first and second controllable light sources and optical receiver means for producing an electrical signal in response to the reception of light from said sources comprising:
   means for producing a first frequency signal modulated by a second frequency, and a third frequency signal modulated by said second frequency;
   means for energizing said first light source in response to said first modulated signal and for energizing said second light source in response to said third modulated signal;
   means responsive to said electrical signal for producing a fourth signal including said first frequency signal components and for producing a fifth signal including said third frequency signal components; and
   means for demodulating said fourth and fifth signals.

2. The oximeter system of claim 1, wherein said electrical signal includes physiological information signals; and
   wherein said fourth and fifth signals exhibit a band of frequencies corresponding to said band of physiological information signals.

3. The oximeter of claim 2, wherein said fourth and fifth signal producing means includes tuned circuit means resonant at said first and third frequencies.

4. The oximeter of claim 3, wherein said demodulating means comprises amplitude demodulating means responsive to reference signals including said first and third frequencies for producing physiological information signals.

5. An oximeter system comprising:
   means for producing first and second carrier signals;
   means for amplitude modulating said carrier signals in a time interleaved manner;
   first and second controllable light sources which are respectively controlled by said modulated carrier signals;
   means responsive to light from said source which has been subjected to a physiological phenomenon for producing an electrical signal containing said carrier signals and physiological information signals;
   means for separating said carrier signals and physiological information signals from undesired signal components; and
   means for demodulating said carrier signals and physiological information signals to recover said physiological information.

6. An oximeter system, including at least one controllable light source and optical receiver means for producing an electrical signal in response to the reception of light from said source comprising:
   a source of frequency reference signals;
   means for producing a modulated waveform;
   means for coupling said reference signals to said modulated waveform producing means in a direct-current isolated manner;
   means for energizing said light source in response to said modulated waveform;
   demodulator means for demodulating components of said electrical signal containing a frequency of said modulated waveform; and
   means for coupling said electrical signal to said demodulator means in a direct-current isolated manner.

7. The oximeter system of claim 6, further comprising means, responsive to said electrical signal, for separating components of said electrical signal containing a frequency of said modulated waveform.

8. The oximeter of claim 7, wherein said separating means comprises a tuned circuit.

9. The oximeter of claim 7, wherein said electrical signal coupling means comprises a transformer, and said separating means comprises a resonant winding of said transformer.

* * * * *